United States Patent [19]  [11] 4,416,830
Morr et al.  [45] Nov. 22, 1983

[54] POLYETHER PHOSPHORIC ACIDS OR ESTERS

[75] Inventors: Michael Morr, Braunschweig; Maria-Regina Kula, Wolfenbüttel, both of Fed. Rep. of Germany

[73] Assignee: Gesellschaft fur Biotechnologische Forschung mbH (GBF), Braunschweig-Stockheim, Fed. Rep. of Germany

[21] Appl. No.: 243,949

[22] PCT Filed: Aug. 28, 1980

[86] PCT No.: PCT/EP80/00085
§ 371 Date: Mar. 3, 1981
§ 102(e) Date: Mar. 3, 1981

[87] PCT Pub. No.: WO81/00571
PCT Pub. Date: Mar. 5, 1981

[30] Foreign Application Priority Data

Aug. 30, 1979 [DE] Fed. Rep. of Germany ....... 2935134
Oct. 24, 1979 [DE] Fed. Rep. of Germany ....... 2943016

[51] Int. Cl.³ .......................... C07F 9/09; C07F 9/165
[52] U.S. Cl. .......................... 260/929; 260/502.4 R; 260/507.4 P; 260/941; 260/944; 260/950; 556/405
[58] Field of Search ............... 260/929, 950, 941, 944, 260/507.4 R, 507.4 P

[56] References Cited

U.S. PATENT DOCUMENTS

| 2,632,767 | 3/1953 | Smith, Jr. et al. | 260/929 |
| 2,853,471 | 9/1958 | Beadell | 260/950 |
| 3,032,578 | 12/1962 | MacMullen et al. | 260/951 |
| 3,277,217 | 10/1966 | Nehmsmann et al. | 260/950 |
| 3,340,329 | 4/1967 | Guarnaccio et al. | 260/925 |
| 3,428,456 | 9/1969 | Grabhöfer et al. | 96/87 |
| 4,056,480 | 11/1977 | Herber | 260/929 |
| 4,154,674 | 3/1979 | Warshawsky et al. | 210/32 |
| 4,220,611 | 9/1980 | Wolf | 260/929 |
| 4,343,735 | 8/1982 | Menge et al. | 260/112 R |

FOREIGN PATENT DOCUMENTS

| 1103031 | 11/1961 | Fed. Rep. of Germany . | |
| 1156563 | 4/1963 | Fed. Rep. of Germany . | |
| 2314243 | 8/1977 | France . | |
| 954792 | 4/1964 | United Kingdom | 260/929 |
| 954793 | 4/1964 | United Kingdom | 260/929 |
| 1424513 | 2/1976 | United Kingdom | 260/929 |

Primary Examiner—Anton H. Sutto
Attorney, Agent, or Firm—Hammond & Littell, Weissenberger and Muserlian

[57] ABSTRACT

This invention relates to phosphorus-containing compounds having the formula:

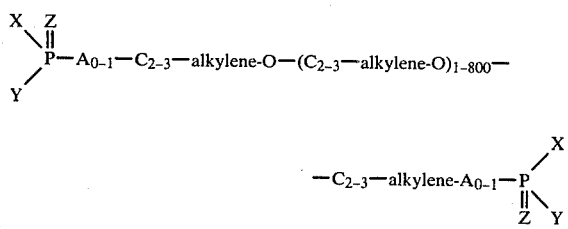

wherein A=O or S, Z=O or S and X and Y=various substituents.

5 Claims, No Drawings

POLYETHER PHOSPHORIC ACIDS OR ESTERS

The invention relates to compounds of the general formula

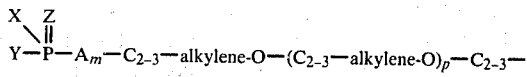
$$Y-P-A_m-C_{2-3}-\text{alkylene-O}-(C_{2-3}-\text{alkylene-O})_p-C_{2-3}-$$

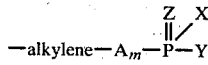
$$-\text{alkylene}-A_m-P-Y$$

wherein (a1)
- p = 1 to 800 and
- m = 1,
- A = an oxygen atom,
- X = a chlorine atom or a hydroxyl group,
- Y = X or an alkoxy radical having 1 to 5 carbon atoms,
- Z = an oxygen or sulphur atom; or (a2)
- m = 1,
- A = an oxygen atom,
- X = an alkoxy radical having 1 to 5 carbon atoms, a phenylalkoxy radical having 0 to 5 carbon atoms in the alkylene group, an alkylamino radical having 1 to 5 carbon atoms, a dialkylamino radical having 1 to 5 carbon atoms in each of the alkyl groups, a phenylalkylamino radical having 0 to 5 carbon atoms in the alkylene group, a bisphenylalkylamino radical having 0 to 5 carbon atoms in each of the alkylene groups, or a p-nitrophenoxy radical, it being possible for the phenyl groups of the phenylalkoxy radicals, phenylalkylamino radicals and bisphenylalkylamino radicals to be substituted by a hydroxyl radical, by an alkyl radical having 1 to 5 carbon atoms or by an alkoxy radical having 1 to 5 carbon atoms,
- Y = X or an alkoxy radical having 1 to 5 carbon atoms, and
- Z = an oxygen atom; or (a3)
- m = 1,
- A = an oxygen atom,
- X = a hydroxyl radical,
- Y = an alkylthio radical having 1 to 5 carbon atoms, an aminoalkylthio radical having 2 to 5 carbon atoms or a carboxyalkylthio radical having 1 to 5 carbon atoms in the alkylene group, and
- Z = an oxygen atom; or (b)
- m = 1,
- A = a sulphur atom,
- X = Y = a hydroxyl radical and
- Z = an oxygen atom; or (c)
- m = 0,
- X = Y = a hydroxyl radical, an alkoxy radical having 1 to 5 carbon atoms, a phenylalkoxy radical having 0 to 5 carbon atoms in the alkylene group, it being possible for the phenyl group to be substituted by a hydroxyl radical, by an alkyl radical having 1 to 5 carbon atoms or by an alkoxy radical having 1 to 5 carbon atoms, or a trialkylsilyloxy radical having 1 to 5 carbon atoms in the alkyl groups, and
- Z = an oxygen atom, and their derivatives in which one of the two

$$Y-P-A_m-$$

groups is replaced by an alkoxy group having 1 to 5 carbon atoms, and the alkali metal salts and salts with ammonia and with amines, of the acids of phosphorus and of the carboxylic acids.

The polyether chain of the above compounds is made up of ethylene glycol, propylene glycol or i-propylene glycol units or of more than one of these units; in this case p can have a value of 3 to 250 and preferably of 30 to 160.

Examples of alkoxy radicals are the methoxy, ethoxy and propoxy radicals. Examples of optionally nuclear-substituted phenylalkoxy radicals are optionally nuclear-substituted alkoxy radicals having 0 or 1 carbon atom in the alkylene group. Examples of alkylamino and dialkylamino radicals are the methylamino, ethylamino and propylamino radicals and the dimethylamino, diethylamino and dipropylamino radicals, respectively. Examples of optionally nuclear-substituted phenylalkylamino and bisphenylalkylamino radicals are optionally nuclear-substituted phenylalkylamino and bisphenylalkylamino radicals, respectively, having 0 or 1 carbon atom in the alkylene group. Examples of alkylthio radicals are alkylthio radicals having 1 to 3 carbon atoms. Examples of aminoalkylthio radicals are aminoalkylthio radicals having 2 or 3 carbon atoms. Examples of carboxyalkylthio radicals are carboxyalkylthio radicals having 1 to 3 carbon atoms in the alkylene group. An example of a trialkylsilyloxy radical is the trimethylsilyloxy radical.

The nuclear substituents of the nuclear-substituted phenylalkoxy, phenylalkylamino and bisphenylalkylamino radicals may be methyl, ethyl, propyl, methoxy, ethoxy and/or propoxy radicals.

The salts are preferably salts of the acids of phosphorus, preferably ammonium, lithium, sodium or potassium salts.

Polyethylene glycol, polypropylene glycol, poly-i-propylene glycol or their copolymers may be used as starting materials for the manufacture of all the compounds. Methods of manufacture are described below.

(I) Manufacture of compounds of the general formula where m = 1; A = an oxygen atom; X = a chlorine atom or a hydroxyl radical; Y = X or an alkoxy radical having 1 to 5 carbon atoms; Z = an oxygen atom For the manufacture of phosphoric acid halides, a polyethylene glycol can be reacted with phosphorus oxychloride or pyrophosphoryl chloride with or without a solvent, such as a phosphoric acid trialkyl ester, for example triethyl phosphate, or dichloromethane, in the presence of an acid-binding agent, for example a tertiary base, such as triethylamine or pyridine, or in the presence of a molecular sieve (of, for example, 0.4 nm). The phosphoric acid halides obtained can be hydrolysed with water or firstly with half the stoichiometric quantity of a $C_{1-5}$-alcohol and then with water to form the free phosphoric acids.

The free phosphoric acids can also be obtained directly by reacting with a mixture of phosphorus pentoxide and 85% phosphoric acid (condensed phosphoric acids) in the molten state. The reaction mixture can be worked up by hydrolysis and recrystallisation from absolute ethanol.

(II) Manufacture of compounds of the general formula wherein $m=1$; $A=$ an oxygen atom; $X=Y=$ a chlorine atom or a hydroxyl radical; $Z=$ a sulphur atom Such compounds are obtained by reacting, for example, a polyalkylene glycol with thiophosphoryl chloride in a solvent, for example in a phosphoric acid trialkyl ester, such as triethyl phosphate. The halide obtained can be saponified, for example at a pH of approximately 7 in the presence of lithium hydroxide. The free acid can be liberated from the lithium salt in the usual manner.

(III) Manufacture of compounds of the general formula wherein $m=1$; $A=$ an oxygen atom; $X=Y=$ an alkoxy radical having 1 to 5 carbon atoms, an optionally nuclear-substituted phenylalkoxy radical having 0 to 5 carbon atoms in the alkylene group, an alkylamino or dialkylamino radical having 1 to 5 carbon atoms in the alkyl radical, an optionally nuclear-substituted phenylalkylamino or bisphenylalkylamino radical having 0 to 5 carbon atoms in the alkylene group, a p-nitrophenoxy radical; $Z=$ an oxygen atom The esters can be obtained either by esterifying in the usual manner the free phosphoric acids obtained according to (I) or directly by reacting with alcohols the phosphoric acid halides obtained according to (I). If the phosphoric acid halides obtained according to (I) are reacted with amines the phosphoric acid amides are obtained.

(IV) Manufacture of compounds of the general formula wherein $m=1$; $A=$ an oxygen atom; $X=$ a hydroxyl radical; $Y=$ an alkylthio radical having 1 to 5 carbon atoms, an aminoalkylthio radical having 2 to 5 carbon atoms, a carboxyalkylthio radical having 1 to 5 carbon atoms in the alkylene group; $Z=$ an oxygen atom The compounds with alkylthio radicals can be obtained, for example, by reacting the compounds obtained according to (II) and having terminal $(LiO)_2P(S)$—O— radicals, with a trialkyl phosphate in an aqueous medium. By reacting the mentioned compounds obtained according to (II) with an aminoalkyl halide having 2 to 5 carbon atoms or with its hydrohalide, the compounds having aminoalkylthio radicals are obtained. For example, it is possible to use an ω-bromoalkylamine or its hydrobromide. Accordingly, by reaction with a halocarboxylic acid having 1 to 5 carbon atoms in the alkylene chain, for example bromoacetic acid, the compounds having carboxyalkylthio radicals are obtained. In all three cases, therefore, the $(LiO)_2P(S)$—O— radical is alkylated at the sulphur atom.

(V) Manufacture of compounds of the general formula wherein $m=1$; $A=$ a sulphur atom; $X=Y=$ a hydroxyl radical; $Z=$ an oxygen atom For the manufacture of such compounds, a polyalkylene glycol can be reacted with a thionyl halide, for example thionyl bromide, in a solvent in the presence of an amine, for example in toluene in the presence of triethylamine. The resulting dihalide having terminal halogen atoms can be reacted in an Åkerfeldt reaction to form compounds having $(O^-)_2P(O)$—S— radicals, for example with $(LiO)_3PS$ in a water/DMF mixture. The free acid can be obtained in known manner from the resulting compound.

(VI) Manufacture of compounds of the general formula wherein $m=0$; $X=Y=$ a hydroxyl radical, an alkoxy radical having 1 to 5 carbon atoms, an optionally nuclear-substituted phenylalkoxy radical having 0 to 5 carbon atoms in the alkylene group, a trialkylsilyloxy radical having 1 to 5 carbon atoms in the alkyl groups; $Z=$ an oxygen atom For the manufacture of such compounds a polyether obtained according to (V) and having terminal halogen atoms can be subjected to a Michaelis-Arbusov reaction and reacted with a trialkyl phosphite to form phosphonic acid esters. Such esters can also be obtained by means of a Michaelis-Becker reaction in which a polyether having terminal halogen atoms is reacted with alkali metal phosphorous acid dialkyl esters, for example sodium phosphorous acid dialkyl esters, in a solvent, such as benzene, toluene or an alcohol. The esters obtained can be saponified directly with acids, for example concentrated hydrochloric acid, to form the free phosphonic acids. The free phosphonic acids can, however, also be obtained firstly by reacting the phosphonic acid esters with a trialkylsilyl halide, for example with trimethylsilyl chloride or bromide, and then saponifying with water. This method of saponification is milder than saponification by means of acids. In the Michaelis-Arbusov reaction an optionally nuclear-substituted triphenyl phosphite may be used instead of trialkyl phosphite.

(VII) Manufacture of compounds of the general formula, in which compounds one of the two YXP(Z)—O— groups is replaced by an alkoxy group having 1 to 5 carbon atoms Such compounds are obtained by using polyalkylene glycols in which one of the terminal OH radicals is etherified by a $C_{1-5}$-alkyl group as starting materials.

(VIII) Manufacture of salts of carboxylic acids and acids of phosphorus from compounds of the general formula Insofar as such salts have not already been discussed above they are obtained by customary neutralisation.

The phosphorus-containing polyalkylene glycol derivatives that have

or HOOC radicals, can be used as liquid cation exchangers, for example for purifying proteins or glycoproteins in two-phase systems. In addition, the phosphorus-containing polyalkylene glycol derivatives can be used in cosmetics, pharmacy and the food industry and, in particular, the esters can be used as plant- and timber-protecting agents.

The invention is explained in more detail below by means of Examples.

EXAMPLE 1

Manufacture of bisphosphoric acid dichloride polyethylene glycol monoester and bisphosphoric acid polyethylene glycol monoester $m=1$; $A=O$ atom; $X=Y=Cl$ atom or OH radical; $Z=O$ atom.

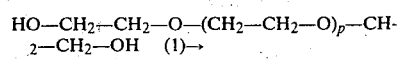

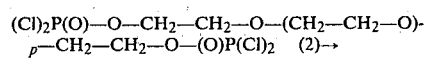

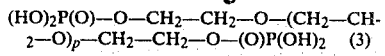

100 g (16.7 mmol) of PEG (average molecular weight 6000; Serva) were dried for two hours in a round-bottomed flask at 60° C. in an oil pump vacuum. The PEG was then dissolved at 50° C. in 250 ml of phosphoric acid triethyl ester that had been freshly distilled and stored over a molecular sieve. With the exclusion of atmospheric moisture, 25.6 g (15.3 ml=0.1669 mol) of phosphorus oxychloride were added dropwise in the course of 30 minutes. The mixture was stirred for 6 hours at 50° C., the reaction mixture becoming slightly brown.

Under a water-jet vacuum and then under an oil pump vacuum, first the excess phosphorus oxychloride and then the phosphoric acid triethyl ester were removed from the reaction mixture and used for further reactions. The intermediate product (2) was hydrolysed in the course of 2 hours at room temperature by the addition of 500 ml of water. After concentration in a rotary evaporator, a viscous brown oil was obtained that was dissolved in 1 liter of water and treated with 20 g of active carbon (Merck). After filtering, concentration to dryness was again effected, the residue was dissolved in 1 liter of absolute denatured ethanol and treated again with 20 g of active carbon. Filtration was effected through a frit coated with kieselguhr (Serva) and the product was left to crystallise out overnight at 4° C. The colourless crystal mass was suction-filtered, washed with ether (DAB 7) and dried in a vacuum desiccator. Weight of dry compound (3): 90 g.

Characterisation:
1. Recording of the titration curve; OH radicals substituted to the extent of 90 to 100% by phosphate radicals
2. $^{31}$P spectrum; 1 signal at 0.1 ppm
3. Phosphate determination after decomposition
4. The aqueous solution of compound (3) contained neither chloride nor free phosphate.

EXAMPLE 2

Manufacture of bisphosphoric acid dichloride polyethylene glycol monoester and bisphosphoric acid polyethylene glycol monoester m=1; A=O atom; X=Y=Cl atom or OH radical; Z=O atom 130 g (84.4 mmol) of PEG (average molecular weight 1540; Riedel de Haen) were dried for 2 hours at 50° C. under an oil pump vacuum and then dissolved in 250 ml of triethyl phosphate at 40° C. With the exclusion of moisture and while stirring, 40 ml (425 mmol) of phosphorus oxychloride were added dropwise in the course of 30 minutes. After 3 hours the excess phosphorus oxychloride was drawn off under a water-jet vacuum at 40° C. for 1 hour and then, under an oil pump vacuum, the triethyl phosphate was drawn off in the course of 3 hours. Hydrolysis was effected for 5 hours at 4° C. with 2 liters of water. Concentration was effected in a rotary evaporator, water was added to the oily residue three times in a quantity of 100 ml each time and concentration was effected again. The slightly yellowish residue was dissolved in 1 liter of absolute denatured ethanol and left to stand overnight at 4° C. After suction-filtering the crystal mass, washing was effected with cold ethanol and ether, and drying was effected in a vacuum desiccator. Weight of the dry phosphate-polyethylene glycol-phosphate: 122 g.

Characterisation: cf. Example 1

1. $^{31}$P spectrum: 0.2 ppm
2. The substance did not contain free phosphate and was free of chloride.

EXAMPLE 3

Manufacture of compounds of the general formula wherein m=1; A=O atom; X=Y=Cl atom or OH radical; Z=S atom; or the salts thereof

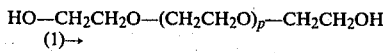

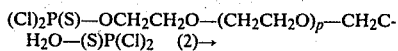

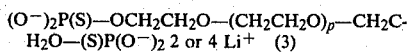

60 g (10 mmol) of PEG (average molecular weight 6000; Serva) were dried at 50° C. for 2 hours under an oil pump vacuum. After dissolving in 150 ml of triethyl phosphate, 5.2 ml (50 mmol) of thiophosphoryl chloride were added dropwise at 50° C. in the course of 30 minutes with the exclusion of moisture and while stirring. After stirring for 5 hours, excess thiophosphoryl chloride was drawn off under a water-jet vacuum for 1 hour and then triethyl phosphate was drawn off under an oil pump vacuum. The intermediate product (2) was hydrolysed with 300 ml of water at pH 7 by adding a 2 M LiOH solution (pH Stat). After concentration in a rotary evaporator, the residue was dissolved in 600 ml of denatured absolute ethanol and left to stand overnight at 4° C. The crystal mass was suction-filtered and washed with ice-cold ethanol and ether. After drying in a vacuum desiccator, 55 g of polyethylene glycol thionophosphate (3) were obtained as a lithium salt.

Characterisation:
1. Compound (3) did not contain any free thionophosphate and was free of chloride.
2. Degree of substitution 90 to 100%.
3. $^{31}$P spectrum: 43.41 ppm.

EXAMPLE 4

Manufacture of compounds of the general formula wherein m=1; A=O atom; X=OH radical; Y=methylthio radical, carboxymethylthio radical or ω-aminoethylthio radical; Z=O atom; or the salts thereof

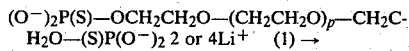

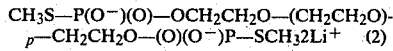

A. 6 g (approximately 1 mmol) of compound (1) were dissolved in 50 ml of water and 10 ml of trimethyl phosphate were added. During the reaction the pH value was maintained at 7.5. The course of the reaction could be followed well using a silver nitrate solution. Whereas compound (1) reacts with silver nitrate in a nitric acid solution to give a brown colouration, compound (2) does not yield any colouration. The reaction was complete after approximately 4 hours at room temperature. Concentration was effected in a rotary evaporator under a water-jet vacuum and an oil pump vacuum and the residue was crystallised from denatured absolute ethanol. After suction-filtering the crystal mass, washing with ether and drying in a vacuum desiccator, 5 g of compound (2) were obtained. The reaction was quantitative.

Characterisation:

$^{31}$P spectrum: the structure was clearly verified by a signal at 22.32 ppm.

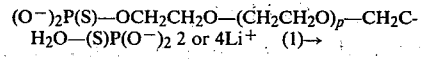

$(O^-)_2P(S)$—$OCH_2CH_2O$—$(CH_2CH_2O)_p$—$CH_2C$-$H_2O$—$(S)P(O^-)_2$   2 or 4Li$^+$   (1)→

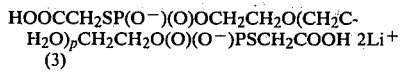

HOOCCH$_2$SP(O$^-$)(O)OCH$_2$CH$_2$O(CH$_2$C-H$_2$O)$_p$CH$_2$CH$_2$O(O)(O$^-$)PSCH$_2$COOH  2Li$^+$
(3)

B. 3 g (approximately 0.5 mmol) of compound (1) were dissolved in 100 ml of water and 500 mg of bromoacetic acid were added at room temperature. The pH value of the reaction solution was maintained at 7.5. The reaction was complete after approximately 2 hours (no brown colouration with silver nitrate solution). The mixture was freed from salt by dialysis. After lyophilising the aqueous solution, approximately 2.5 g of compound (3) were obtained. The reaction was quantitative.

Characterisation:

$^{31}$P spectrum: the structure was clearly verified by a signal at 20.5 ppm.

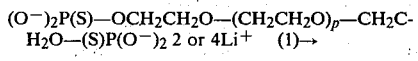

$(O^-)_2P(S)$—$OCH_2CH_2O$—$(CH_2CH_2O)_p$—$CH_2C$-$H_2O$—$(S)P(O^-)_2$   2 or 4Li$^+$   (1)→

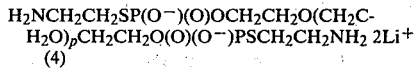

H$_2$NCH$_2$CH$_2$SP(O$^-$)(O)OCH$_2$CH$_2$O(CH$_2$C-H$_2$O)$_p$CH$_2$CH$_2$O(O)(O$^-$)PSCH$_2$CH$_2$NH$_2$  2Li$^+$
(4)

C. 6 g (approximately 1 mmol) of compound (1) were dissolved in 100 ml of water and 470 mg of 2-bromoethylammonium bromide were added at room temperature. The pH value of the reaction solution was maintained at 7.5 by the addition of 0.2 N NaOH. The reaction was complete after 5 hours (no brown colouration with silver nitrate solution). After concentration in a rotary evaporator the residue was crystallised from denatured absolute ethanol. After suction-filtering the crystal mass, washing with ether and drying in a vacuum desiccator, approximately 5 g of compound (4) were obtained. The reaction was again quantitative.

Characterisation:

$^{31}$P spectrum: the structure was clearly verified by a signal at 19.2 ppm.

EXAMPLES 5 TO 8

Manufacture of compounds of the general formula wherein m=0; X=Y=ethoxy radical; Z=O atom

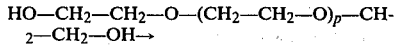

HO—CH$_2$—CH$_2$—O—(CH$_2$—CH$_2$—O)$_p$—CH$_2$—CH$_2$—OH→

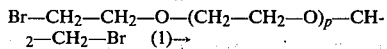

Br—CH$_2$—CH$_2$—O—(CH$_2$—CH$_2$—O)$_p$—CH$_2$—CH$_2$—Br   (1)→

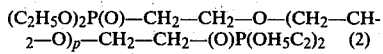

(C$_2$H$_5$O)$_2$P(O)—CH$_2$—CH$_2$—O—(CH$_2$—CH$_2$—O)$_p$—CH$_2$—CH$_2$—(O)P(OH$_5$C$_2$)$_2$   (2)

Polyethylene glycols (molecular weight 1540, 6000, 10,000 and 20,000) were reacted in known manner, in toluene in the presence of triethylamine, with thionyl bromide; cf. Johansson, G., Biochim. Biophys. Acta, 222 to 381 (1970) and Johansson, G., Hartman, A. and Albertsson, P.-A., Eur. J. Biochem., 33, 379 to 386 (1973).

10 ml of triethyl phosphite (excess) were added to 6 g of bisbromopolyethylene glycol (average molecular weight 6000; Serva; or a corresponding quantity of the other bisbromine compounds of the polyethylene glycols indicated above) in a round-bottomed flask. The mixture was refluxed for 24 hours (air cooling) with the exclusion of moisture; the mixture was then allowed to cool and 50 ml of ether were added. The mixture was filtered off using a frit and excess triethyl phosphite was removed by washing with ether. After drying in a vacuum desiccator, approximately 6 g of compound (2) were obtained. Traces of triethyl phosphite were removed under an oil pump vacuum. The reaction was quantitative. After the reaction, the bromine content was less than 0.05%.

Characterisation of the compounds (2):

1. $^{31}$P spectrum:

| average PEG molecular weight | 1540 | 6000 | 10,000 | 20,000 |
|---|---|---|---|---|
| signal (ppm) | 32.1 | 32.14 | 32.1 | 32.1 |

2. degree of substitution: depended on the degree of bromination which in the case of the individual polyethylene glycols was between 60 and 100%

EXAMPLE 9

Manufacture of compounds of the general formula wherein m=0; X=Y=ethoxy radical; Z=O atom; one of the two YXP(Z)—A$_m$— groups is replaced by a methoxy group

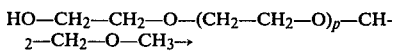

HO—CH$_2$—CH$_2$—O—(CH$_2$—CH$_2$—O)$_p$—CH$_2$—CH$_2$—O—CH$_3$→

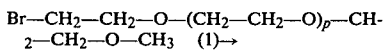

Br—CH$_2$—CH$_2$—O—(CH$_2$—CH$_2$—O)$_p$—CH$_2$—CH$_2$—O—CH$_3$   (1)→

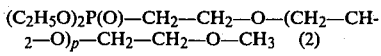

(C$_2$H$_5$O)$_2$P(O)—CH$_2$—CH$_2$—O—(CH$_2$—CH$_2$—O)$_p$—CH$_2$—CH$_2$—O—CH$_3$   (2)

The method was the same as in Examples 5 to 8 except that monomethoxypolyethylene glycol was used instead of polyethylene glycol as the starting material (average molecular weight 5000).

Characterisation of the compound:

$^{31}$P spectrum: 32.1 ppm.

EXAMPLES 10 TO 13

Manufacture of compounds of the general formula wherein m=0; X=Y=trimethylsilyloxy radical or hydroxyl radical; Z=O atom

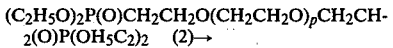

(C$_2$H$_5$O)$_2$P(O)CH$_2$CH$_2$O(CH$_2$CH$_2$O)$_p$CH$_2$CH$_2$(O)P(OH$_5$C$_2$)$_2$   (2)→

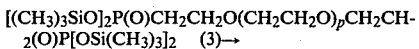

[(CH$_3$)$_3$SiO]$_2$P(O)CH$_2$CH$_2$O(CH$_2$CH$_2$O)$_p$CH$_2$CH$_2$(O)P[OSi(CH$_3$)$_3$]$_2$   (3)→

(HO)$_2$P(O)CH$_2$CH$_2$O(CH$_2$CH$_2$O)$_p$CH$_2$CH$_2$(O)P(OH)$_2$   (4)

24 g of compound (2) of Examples 5 to 8 (average PEG molecular weight 6000; corresponding quantities of the other, analogous compounds (2) of Examples 5 to 8) were dissolved in 150 ml of anhydrous dichloromethane and 3.5 ml of bromotrimethylsilane (excess; Aldrich) were added with the exclusion of moisture. The mixture was left to stand for 12 hours, 2 days or longer at room temperature, then concentrated in a rotary evaporator and 500 ml of water were added. The whole was stirred for 5 hours or overnight, concentrated again and recrystallised from ethanol. The yield of compound (4) was 17 g (average PEG molecular weight 6000).

Characterisation:
1. $^{31}P$ spectra:

| average PEG molecular weight | 1,540 | 6,000 | 10,000 | 20,000 |
|---|---|---|---|---|
| signal (ppm) | 26.5 | 25.9 | 25.9 | 25.9 |

2. $^{13}C$ spectrum: for compounds (4) having an average PEG molecular weight of 1540, the structure was additionally confirmed by a spectrum of this type.

EXAMPLE 14

Manufacture of compounds of the general formula wherein m=0; X=Y=trimethylsiloxy group or hydroxyl group; Z=O atom; one of the two YXP(-Z)—$A_m$— groups is replaced by a methoxy group Examples 10 to 13 were repeated except that compound (2) of Example 9 was used.

Characterisation:
$^{31}P$ spectrum: 26.00 ppm

EXAMPLE 15

Manufacture of compounds of the general formula wherein m=1; A=S—atom; X=Y=OH; Z=O atom; or their salts Br—CH$_2$CH$_2$O—(CH$_2$CH$_2$O)$_p$—CH$_2$CH$_2$—Br
(1)—

(O$^-$)$_2$P(O)—S—CH$_2$CH$_2$O—(CH$_2$CH$_2$O)-$_p$—CH$_2$CH$_2$—S—(O)P(O$^-$)$_2$ (3)

1.6 g (approximately 1 mmol) of compound (1) were dissolved in 20 ml of water, and 5 ml of dimethylformamide and 250 mg of trilithium thionophosphate were added (pH 11.7). The course of the reaction was followed with silver nitrate in a nitric acid solution. After 24 hours, 150 mg of trilithium thionophosphate were added (ph 10.6). After 3 days (pH 8.5) the mixture was concentrated to dryness in a rotary evaporator, compound (3) was dissolved in 50 ml of dichloromethane and the salt was separated off. The dichloromethane solution was concentrated and the residue was lyophilised from water. The yield was 1.2 g.

Characterisation:
$^{31}P$ spectrum: the structure of compound (3) was clearly verified by a signal at 16.4 ppm.

We claim:
1. Compounds of the general formula:

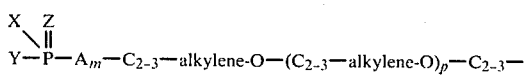

wherein
p=30 to 800 and
(a1)
 m=1,
 A=O atom,
 X=OH and Y=X or —O—C$_{1-5}$-alkyl,
 Z=O or S atom; or
(a2)
 m=1,
 A=O atom
 X=

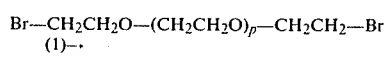

Y=X or —O—C$_{1-5}$-alkyl,
 Z=O atom; or
(a3)
 m=1,
 A=O atom,
 X=OH, Y=—S—C$_{1-5}$-alkyl, —S—C$_{2-5}$-alkyl amine, —S—C$_{1-5}$-alkyl carboxyl,
 Z=O atom; or
(b)
 m=1,
 A=S atom,
 X=Y=OH,
 Z=O atom; or
(c)
 m=0,
 X=Y=OH,

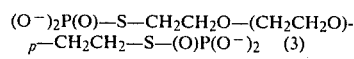

Z=O atom,
and their derivatives in which one of the two

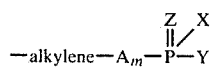

groups is replaced by a C$_{1-5}$ alkoxy group and the alkali metal derivatives and salts with ammonia and amines, of the acids of phosphorus and of the carboxylic acids.

2. Compounds according to claim 1, characterised in that, in the general formula according to claim 1, C$_{2-3}$-alkylene=—CH$_2$—CH$_2$, —CH$_2$—CH$_2$—CH$_2$—, —CH$_2$—CH(CH$_3$)— or mixtures thereof; p=30 to 160.

3. Compounds according to claim 1 or 2, characterized in that, in the general formula according to claim 1, wherein when Y is —O—C$_{1-5}$-alkyl=methoxy, ethoxy or propoxy,
wherein when X and/or Y is —O—C$_{0-5}$—alkylene—⌬—OH =

—O—C$_{0-1}$—alkylene—⌬—OH wherein when Y is —S—C$_{1-5}$-alkyl=—S—C$_{1-3}$-alkyl,
wherein when Y is —S—C$_{2-5}$-alkyl amine=—S—C$_{2-3}$-alkyl amine
wherein when Y is —S—C$_{1-5}$-alkyl carboxyl=—S—C$_{1-3}$-alkyl carboxyl.

4. Compounds according to claim 1 or 2, characterised by the ammonium, lithium, sodium or potassium salts of said acids of phosphorus.

5. Compounds according to claim 1 or 2 wherein at least one $$\text{HO}-\overset{\overset{\displaystyle\diagdown\|}{}}{P}-$$

group is present.

* * * * *